(12) United States Patent
Playfair et al.

(10) Patent No.: US 6,214,357 B1
(45) Date of Patent: Apr. 10, 2001

(54) TREATMENT OF DIABETES

(75) Inventors: John Hugh Lyon Playfair; Khaled Elased, both of London; Joseph Brian De Souza, Middlesex, all of (GB)

(73) Assignee: Rademacher Group Limited, London (GB)

(*) Notice: Subject to any disclaimer, the term of this patent is extended or adjusted under 35 U.S.C. 154(b) by 0 days.

(21) Appl. No.: 09/254,179

(22) PCT Filed: Sep. 2, 1997

(86) PCT No.: PCT/GB97/02356

§ 371 Date: Nov. 30, 1999

§ 102(e) Date: Nov. 30, 1999

(87) PCT Pub. No.: WO98/09637

PCT Pub. Date: Mar. 12, 1998

(30) Foreign Application Priority Data

Sep. 2, 1996 (GB) .................................. 9618290

(51) Int. Cl.[7] ............................ A61K 39/015; C12N 1/06
(52) U.S. Cl. .................................... 424/272.1; 424/269.1; 424/265.1; 424/400; 424/529; 424/530; 424/531; 435/252.3; 435/258.2; 435/258.1
(58) Field of Search .................... 435/252.3, 258.2, 435/258.1; 424/400, 529, 530, 531, 272.1, 269.1, 265.1

(56) References Cited

U.S. PATENT DOCUMENTS 5,759,551 * 6/1998 Ladd et al. .......................... 424/198.1
6,020,144 * 2/2000 Gueiros-Fiho et al. ............ 435/7.22

FOREIGN PATENT DOCUMENTS

WO 83/02896   9/1983 (WO).

OTHER PUBLICATIONS

Elased et al Infection and Immunity, 62(11, 5157–5160, 1994.*
Elased, K. et al., "Blood–Stage Malaria Infection in Diabetic Mice," *Clin. Exp. Immunol.* 99:440–444 (1995).
Looareesuwan, S. et al., "Quinine and Severe Falciparum Malaria in Late Pregnancy," *The Lancet* 4–8 (1985).
Phillips, R. et al., "Hypoglycaemia and Counterregulatory Hormone Responses in Severe Falciparum Malaria: Treatment With Sandostatin," *Quarterly Journal of Medicine* 86:233–240 (1993).
Shafrir, E., "Development and Consequences of Insulin Resistance: Lessons From Animals With Hyperinsulinaemia," *Diabetes & Metabolism* (Paris) 22:122–131 (1996).
Shalev, O. et al., "Falciparum Malaria–Induced Hypoglycaemia in a Diabetic Patient," *Postgrad. Med. J.* 68 :281–282 (1992).
Sigal, R. and Warram, J., "The Interaction Between Obesity and Diabetes," *Current Opinion in Endocrinology and Diabetes* 3:3–9 (1996).

* cited by examiner

Primary Examiner—Diana Dudash
Assistant Examiner—Shahnam Sharareh
(74) *Attorney, Agent, or Firm*—Skjerven, Morrill, MacPherson, LLP; Emily M. Haliday; Peter K. Seperack

(57) ABSTRACT

The present invention provides methods for using a killed malaria parasite or an extract thereof in the treatment of non-insulin dependent diabetes mellitus (NIDDM).

15 Claims, 2 Drawing Sheets

TREATMENT OF DIABETES

The present invention relates to treatment of diabetes mellitus, specifically treatment of non-insulin dependent diabetes mellitus.

Diabetes is sub-divided on clinical grounds into insulin-dependent and non-insulin dependent diabetes mellitus (IDDM and NIDDM respectively, also known as Type 1 and Type 2 respectively). The two forms of the disease are distinguished by a number of features.

In IDDM there is profound insulin deficiency such that even the low levels of insulin which would normally prevent lipolysis and cytogenesis cannot be sustained. Without replacement of insulin, IDDM patients become ketotic and die. IDDM patients therefore generally show high levels of glucose and low levels of insulin. As IDDM progresses, the pancreatic islets are damaged or destroyed, and less and less insulin can be produced.

NIDDM is a common and complex disorder which results from a combination of defects in insulin secretion and impaired insulin sensitivity in peripheral tissues. NIDDM is characterized by hyperglycaemia in both the fasted and fed states, variable degrees of hyperinsulinaemia and obesity. Current therapy includes diet, sulphonylurea to enhance insulin secretion, insulin itself, and biguanides to reduce insulin resistance. There is a need for new antidiabetic agents, since biguanides are quite toxic while sulphonylurea is ineffective in patients with severely impaired islet cell function, and after 10 years of treatment, 50% of patients will have become resistant.

Clinically, the two forms of diabetes are often viewed as two different diseases, and entirely separate treatments are needed for the two forms. In general treatments for the two forms of the disease do not overlap.

In humans, the normal level of glucose in the blood is about 7 mmol/l. Patients are said to be hypoglycaemic at levels of less than about 2.2 mmol/l and hyperglycaemic at levels of above about 10–11 mmol/l.

One of the complications of malaria infection is hypoglycaemia, although the mechanism responsible has not been firmly established. In patients treated with quinine, the drop in glucose levels is often attributed to the hyperinsulinaemic action of quinine, for example by Phillips et al in Q.J. Med. 1993 volume 86, pp 233–240. A few cases in which hypoglycaemia and hyperinsulinaemia preceded treatment with quinine have been reported, for example by Looareesuwna et al in Lancet 1985 ii:4–8.

A single case of a diabetic patient who contracted malaria is reported by Shalev et al in Postgrad. Med. J. 1992 vol. 68, pp 281–282. The patient still became hypoglycaemic during the course of the malaria infection.

Infection of normal mice with blood-stage *P. yoelii* and *P. chabaudi* malaria can induce hypoglycaemia in the normal mice (Elased et al, Clin. Exp. Immunol. 1995, vol. 99, pp 440–444). It is thought that this effect may be due to induction of a burst of insulin which reduces the glucose levels. In the same article, it was reported that malaria infection in insulin-dependent diabetes mellitus (IDDM) induced by administration of streptozotocin induced a profound drop in blood glucose and restored insulin secretion, although severely diabetic mice (again induced by streptozotocin) remained hyperglycaemic with no changes in insulin levels. This supports the theory that the effect is due to induction of a burst of insulin, since mice severely affected with IDDM will have few or no residual islets which can be stimulated to produce insulin.

In NIDDM, the insulin levels are already raised, and there is significant insulin resistance. The inventors have unexpectedly found that administration of malaria parasites to mice which provide a model of human NIDDM will result in lowering of glucose levels. This is entirely unexpected, since previously it was thought that the reduction of glucose levels seen on giving malaria parasites to Type 1 (IDDM) diabetic mice was due to the induction of a burst of insulin. The mechanism of action in NIDDM treatment will inevitably be different.

A further complication of NIDDM is obesity. It has long been known that increasing body weight is associated with increasing levels of insulin resistance, seen in NIDDM. The interaction between obesity and diabetes is explored by Sigal et al in Current Opinion in Endocrinology and Diabetes 1996, volume 3, pp. 3–9. Control of NIDDM can often be achieved by regulation of the diet, and of total food intake. However, this is often unsuccessful as individuals may find it difficult to maintain a diet and to cut food intake.

We have found that administration of malaria parasites or an extract thereof to a mouse model of human NIDDM results in reduced voluntary food intake, with consequent weight loss.

Although not wishing to be bound by this theory, it appears possible that the malaria parasite or extract thereof may act synergistically with the high levels of insulin in the NIDDM sufferer to enhance glucose transport since when normal mice are treated with the killed parasite, the reduction in glucose levels was much less prolonged.

The invention provides the use of killed malaria parasites or an extract thereof in the preparation of a medicament for the treatment of non-insulin dependent diabetes mellitus (NIDDM). The malaria parasite may be any organism responsible for malaria infection. Examples include *Plasmodium yoelii, P. falciparum, P. vinckei, P. vivax, P. chabaudi, P. berghei, P. knowlesi* and *P. coatenyi*. The killed malaria parasites or extracts thereof are particularly effective when collected at the blood stage of infection.

The medicament may be provided in the form of killed malaria parasites or an extract of the parasites, for example fixed in formalin. Other suitable forms include soluble malaria preparations prepared by lysis of parasitised red cells by detergents such as Triton X100 or N-octyl glucoside, which may be followed by fractionation, for example on molecular weight or charge-based columns, and also preparations derived from supernatants of overnight culture of parasitised blood.

The preparation of parasites or the extract can be administered in a variety of dosage forms, for example orally such as in the form of tablets, capsules, sugar- or film-coated tablets, liquid solutions or suspensions or parenterally, for example intramuscularly, intravenously or subcutaneously. The parasites or extracts thereof may therefore be given by injection or infusion.

The dosage of the parasite preparation or the extract depends on a variety of factors including the age, weight and condition of the patient and the route of administration.

It is envisaged that the malaria parasites or active ingredients derived therefrom will be given in a dosage of from $10^7$ to $10^{11}$, preferably $10^8$ to $10^{10}$ parasites or parasite equivalents. By "parasite equivalents" herein is meant the number of parasites needed to prepare an extract.

The killed malaria parasites or the extract may be given to the patient in a single dose, which it is expected will be sufficient to reduce hyperglycaemia for a period of up to 24 hours. Alternatively, lower dosages may be provided a number of times per day, for example 3 or 4 times daily. It is further envisaged that a single, larger dose could be provided for longer term treatment.

The parasites or extracts thereof are formulated for use as pharmaceutical or veterinary compositions also comprising a pharmaceutically or veterinarily acceptable carrier or diluent. The compositions are typically prepared following conventional methods and are administered in a pharmaceutically or veterinarily suitable form.

For example, the solid oral forms may contain, together with the active material, diluents such as lactose, dextrose, saccharose, cellulose, corn starch or potato starch; lubricants such as silica, talc, stearic acid, magnesium or calcium stearate and/or polyethylene glycols; binding agents such as starches, arabic gums, gelatin, methylcellulose, carboxymethylcellulose, or polyvinyl pyrrolidone; disintegrating agents such as starch, alginic acid, alginates or sodium starch glycolate; effervescing mixtures; dye-stuffs; sweeteners; wetting agents such as lecithin, polysorbates, laurylsulphates. Such preparations may be manufactured in known manner, for example by means of mixing, granulating, tabletting, sugar coating, or film-coating processes.

Liquid dispersions for oral administration may be syrups, emulsions and suspensions. The syrups may contain as carrier, for example, saccharose or saccharose with glycerol and/or mannitol and/or sorbitol. In particular a syrup for diabetic patients can contain as carriers only products, for example sorbitol, which do not metabolise to glucose or which only metabolise a very small amount to glucose. The suspensions and the emulsions may contain as carrier, for example a natural gum, agar, sodium alginate, pectin, methylcellulose, carboxymethylcellulose or polyvinyl alcohol.

Suspensions or solutions for intramuscular injections may contain, together with the active compound, a pharmaceutically acceptable carrier such as sterile water, olive oil, ethyl oleate, glycols such as propylene glycol, and, if desired, a suitable amount of lidocaine hydrochloride. Solutions for intravenous injection or infusion may contain a carrier, for example, sterile water which is generally Water for Injection. Preferably, however, they may take the form of a sterile, aqueous, isotonic saline solution. Alternatively, a material may be encapsulated within liposomes.

The invention also relates to a method of treatment of NIDDM which comprises administering to a patient in need thereof a preparation comprising the killed malaria parasites or an extract thereof.

Figure 1:
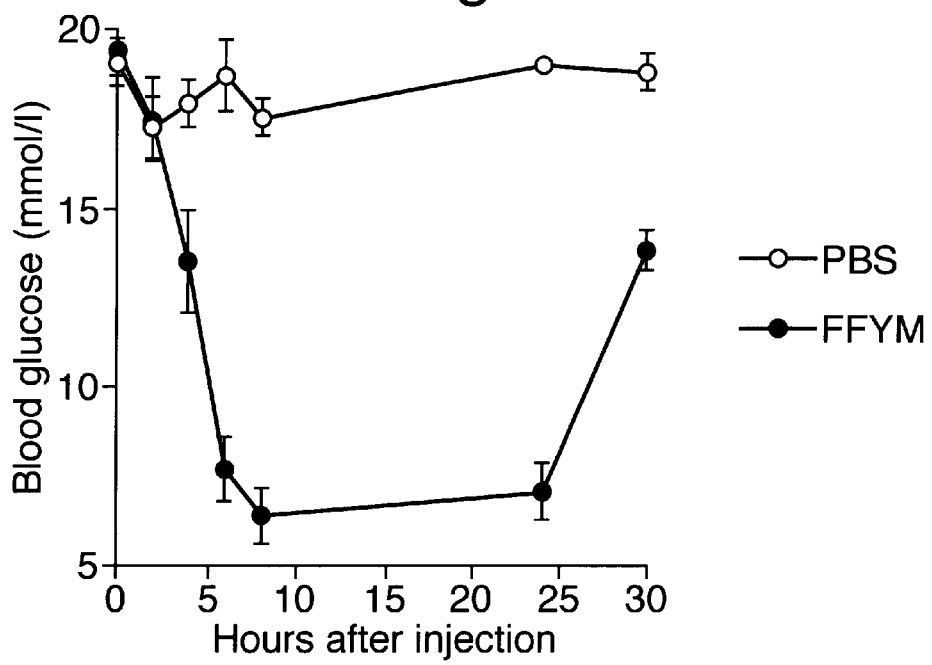
FIG. 1 shows the effect of formalin fixed *P. yoelli* on the blood glucose of obese diabetic mice (aged 10–12 weeks).

The invention is further illustrated by the following examples.

EXAMPLES

Parasites

Infections with the lethal YM line of *Plasmodium yoelii* (FFYM; from Dr. A. Holder, National Institute of Medical Research, London, England) were initiated by i.v. injection of $10^4$ parasitized erythrocytes into normal mice and parasitaemia was determined from blood films stained with Giemsa. In the case of *P. berghei* ANKA (PB; from Dr. N. Wedderburn) $10^6$ parasitized rbc were injected intraperitoneally. *Plasmodium falciparum* (PF) was obtained from Dr. M. Blackman (National Institute of Medical Research, London, England).

Parasitised blood (>90% parasitaemia) was extracted and washed three times in PBS, and the pellet was lysed in 0.01% saponin PBS and washed three times, fixed with 0.06% formalin overnight and washed a further three times before use. This formalin fixed malaria parasite preparation (FFMP) was administered i.v. in saline.

Blood with a parasitaemia of at least 90% was extracted and washed, lysed in 0.01% saponin, and extracted for three hours in 0.5% Triton X100 or 0.7% N-octyl glucoside and then microfuged. The lysate was run on a Sephacryl S.200 column (Pharmacia) and fractions within the first peak (mol. wt. 200–170 kDa) were pooled as Peak 1. Parasite preparations were either injected via the tail vein or fed orally via gastric tube.

Mice

Genetically obese diabetic mice (C57 Bl/Ks db/db) were obtained from Harlan Olac Ltd. Bicester, UK. These mice are a recognised animal model of human NIDDM. Properties of the mice are reviewed by E. Shafrir in Diabetes and Metabolism (Paris) 1996, vol. 22, pp 122–131. The db/db mice are spontaneously hyperphagic insulin oversecretors even before weaning and then become obese and hyperinsulinaemic within the first month of age. Hyperglycaemia develops somewhat later, becoming severe at three to four months. The db/db mice exhibit marked insulin resistance.

The experiments described below were carried out on mice aged 8 to 12 weeks, when both blood glucose and insulin levels are markedly raised (glucose 20.4 mmol/l, insulin 54.9 ng/ml). Normal heterozygous (db/+) litter mates were used as controls (glucose 6.6 mmol/l, insulin 2.8 ng/ml). For some comparisons, normal (C57Bl×Balb/c) F1 mice bred in the animal colony of our laboratory were used.

Measurement of Blood Glucose

Glucose concentrations were determined from a drop of tail blood collected between 10 am and midday, using Glucostix and an Ames Glucometer (Miles Ltd., Stbke Poges, England) according to the manufacturer's instructions. Results in mmol/l are expressed as means±SE.

Determination of Immunoreactive Insulin

Blood was collected from the trunk following decapitation, in heparinized tubes. Plasma was separated by centrifugation and frozen at −20° C. Immunoreactive insulin (IRI) concentrations were determined in 50 $\mu$l volumes in duplicate by the double-antibody radioimmunoassay technique (kit supplied by ICN Biomedicals, Irvine, Calif.) and a crystalline rat insulin standard (Novo Research Institute, Bagsvaerd, Denmark). Plasma insulin in ng/ml is expressed as mean±SE.

Isolation and Incubation of Pancreatic Islets

Islets were isolated from the pancreas of male Sprague-Dawley rats (250–300 g) maintained on a standard light-dark cycle, by a modification of the method of Lacy & Kostianovsky (1967) using collagenase. Two rats were used per assay. Islets were preincubated in batches of 5–6 for 30 min with Krebs bicarbonate buffer (1.0 ml. pH 7.3 to 7.4, 95% $O_2$, $CO_2$, 37° C.) containing 3 mmol/l glucose. The preincubation medium was removed and then replaced with 1.0 ml of Krebs bicarbonate with or without malaria lysate and incubated for a further 60 min. A sample of incubate (200 $\mu$) was removed and stored at −20° C. until assay for insulin.

Statistics

Comparisons were made by Student's t test. Values of P<0.01 were considered significant.

Experiment 1

A single injection of 5×10$^7$ formalin fixed *P. yoelii* (FFYM) parasites was administered to db/db obese mice, a model of type 2, non-insulin dependent diabetes mellitus. A group of nine diabetic (db/db) mice were injected and another group of six left uninjected ("controls"). Blood glucose was measured at 2, 4, 6, 8, 24, and 30 hours as shown in FIG. 1.

It can be seen that the single injection of FFYM lowered the blood glucose from a level or 17 to 18 mmol/l to a normal value of about 7 mmol/l. This normoglycaemia persisted for a period of 24 hours.

Experiment 2

Figure 2:
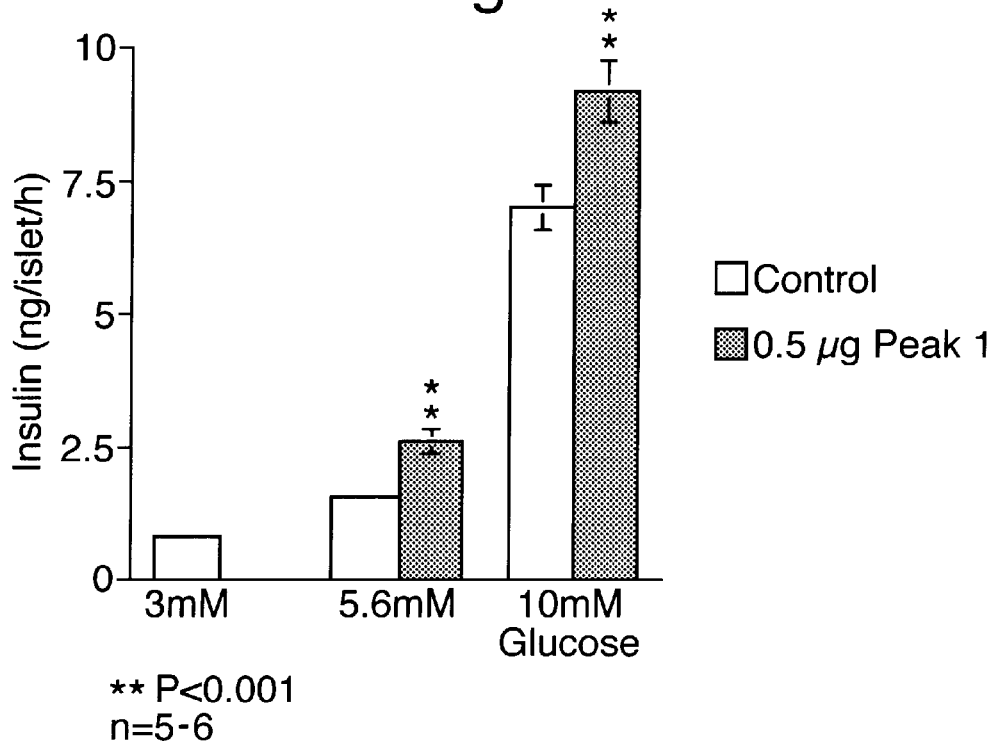
FIG. 2 shows the effect of malaria lysate on insulin secretion from isolated rat pancreatic islets.

A detergent lysate of *P. yoelii* was prepared as described above, and Peak 1 obtained by S.200 fractionation. Addition of this fraction to rat pancreatic islets as described above in the presence of glucose, as described above, stimulated the release of insulin. Results are presented in FIG. 2.

Experiment 3

Figure 3:
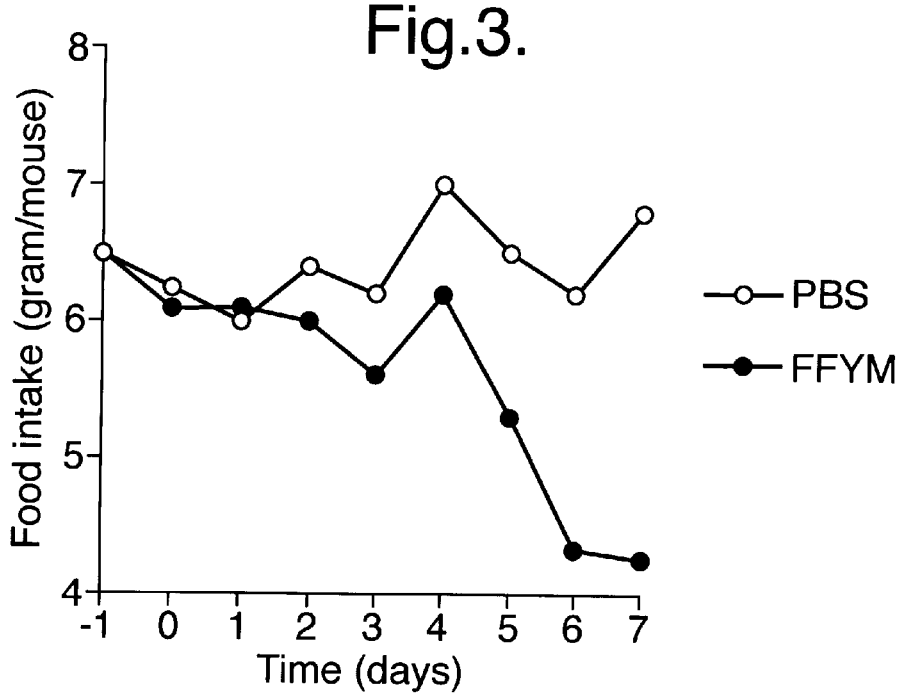
FIGS. 3 and 4 shows the effect of parasite on the food intake and glucose levels respectively, of db/db mice.
Figure 4:
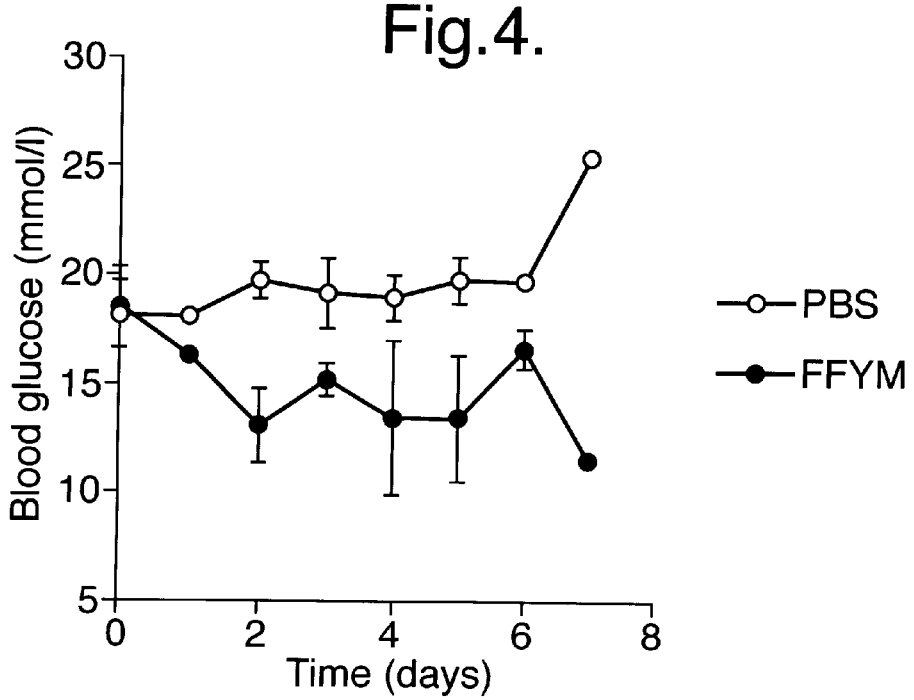

Formalin fixed *P. yoelii* (FFYM) parasites (10$^8$ in 0.2 ml) were given orally to a group of 6 db/db mice, and 0.2 ml of phosphate buffered saline (PBS) to another group. Blood glucose was measured as described above, and the average quantity of food eaten per day was recorded. The mice given the malaria parasites showed a drop in food intake and a significant decrease of blood glucose. Results are shown in FIGS. 3 and 4.

What is claimed is:

1. A method of treatment of NIDDM comprising administering to a patient in need thereof, a preparation comprising a killed malaria parasite or a lysate thereof or a fraction of said lysate.

2. A method according to claim 1, wherein the malaria parasite is selected from the group consisting of *Plasmodium yoelii, P. falciparum, P. vinckei, P. vivax, P. chabaudi, P. berghei, P. knowlesi* and *P. coatneyi*.

3. A method according to claim 1 wherein the malaria parasite is collected at the blood stage of infection.

4. A method according to claim 1 wherein the preparation provides a dosage of from 10$^7$ to 10$^{11}$ parasites or parasite equivalents.

5. A method according to claim 2 wherein the malaria parasite is collected at the blood stage of infection.

6. A method according to claim 2 wherein the preparation provides a dosage of from 10$^7$ to 10$^{11}$ parasites or parasite equivalents.

7. A method according to claim 3 wherein the preparation provides a dosage of from 10$^7$ to 10$^{11}$ parasites or parasite equivalents.

8. A method according to claim 2, wherein the malaria parasite comprises *Plasmodium yoeli*.

9. A method according to claim 2, wherein the malaria parasite comprises *P. falciparum*.

10. A method according to claim 2, wherein the malaria parasite comprises *P. vinckei*.

11. A method according to claim 2, wherein the malaria parasite comprises *P. vivax*.

12. A method according to claim 2, wherein the malaria parasite comprises *P. chabaudi*.

13. A method according to claim 2, wherein the malaria parasite comprises *P. berghei*.

14. A method according to claim 2, wherein the malaria parasite comprises *P. knowlesi*.

15. A method according to claim 2, wherein the malaria parasite comprises *P. coatneyi*.

\* \* \* \* \*